United States Patent [19]
Shiraishi et al.

[11] Patent Number: 5,733,929
[45] Date of Patent: Mar. 31, 1998

[54] PHARMACEUTICAL COMPOSITION FOR TREATING OR PREVENTING ALLERGIC RHINITIS

[75] Inventors: Mitsuru Shiraishi, Amagasaki; Yasuko Ashida, Takatsuki; Tatsumi Matsumoto, Sakai, all of Japan

[73] Assignee: Takeda Chemical Industries, Ltd., Osaka, Japan

[21] Appl. No.: 594,328

[22] Filed: Jan. 30, 1996

Related U.S. Application Data

[63] Continuation of Ser. No. 309,181, Sep. 20, 1994, abandoned.

[30] Foreign Application Priority Data

Sep. 21, 1993 [JP] Japan ................................... 5-235091
Dec. 24, 1993 [JP] Japan ................................... 5-326636

[51] Int. Cl.$^6$ ................................................. A01N 37/00
[52] U.S. Cl. ........................ 514/510; 514/569; 514/570; 514/732; 514/731
[58] Field of Search ................................. 514/510, 569, 514/570, 732, 731

[56] References Cited

PUBLICATIONS

CA105:42484 1986.

*Primary Examiner*—Paul J. Killos
*Attorney, Agent, or Firm*—Wenderoth, Lind & Ponack

[57] ABSTRACT

There is disclosed a pharmaceutical composition for treating or preventing allergic rhinitis which comprises a quinone or hydroquinone derivative having thromboxane $A_2$ receptor antagonism. This compound is hardly inactivated by in vivo metabolism and can maintain its effective blood level for a long term and exhibit excellent pharmacological activity in a low dose.

6 Claims, No Drawings

PHARMACEUTICAL COMPOSITION FOR TREATING OR PREVENTING ALLERGIC RHINITIS

This application is a continuation of now abandoned Ser. No. 08/309,181 filed Sep. 20, 1994, now abandoned.

FIELD OF THE INVENTION

The present invention relates to a pharmaceutical composition for treating or preventing allergic rhinitis which comprises a quinone or hydroquinone derivative having thromboxane $A_2$ receptor antagonism.

BACKGROUND OF THE INVENTION

Allergic rhinitis is a type I allergic disease of nasal mucosa causing paroxysmal and repetitive sneeze, nasal mucus and nasal congestion as three major symptoms. Although antihistamic agents have widely been used to treat and prevent allergic rhinitis, they are not necessarily satisfactory because they are not so effective against nasal congestion of allergic rhinitis and have side effects such as sleepiness, malaise, sedation due to inhibitory action on the central nervous system and cholilytic action. Chemical mediators other than histamine, such as leukotrienes, prostaglandins, platelet-activating factor (PAF) and thromboxane $A_2$, particularly leukotrienes, are believed to be related to nasal congestion on the basis of onset mechanisms of allergic rhinitis (Minoru Okuda, Allergy, Vol. 39, p. 301–306 (1990)).

Compounds having thromboxane $A_2$ receptor antagonism, for example, quinone compounds disclosed in U.S. Pat. No. 5,180,742 and JP-A 63-101322 have been known to be useful as anti-allergic agents, but have never been known to be useful as medicaments for treating and preventing allergic rhinitis.

OBJECTS OF THE INVENTION

The main object of the present invention is to provide a pharmaceutical composition for treating or preventing allergic rhinitis which comprises a quinone or hydroquinone derivative having thromboxane $A_2$ receptor antagonism.

This object as well as other objects and advantages of the present invention will become apparent to those skilled in the art from the following description.

SUMMARY OF THE INVENTION

The present invention provides a pharmaceutical composition for treating or preventing allergic rhinitis which comprises a quinone derivative of the formula (Ia):

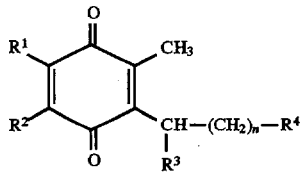

(Ia)

wherein
$R^1$ and $R^2$ are each independently a methyl group or methoxy group, or $R^1$ and $R^2$ are linked together to form —CH=CH—CH=CH—;
$R^3$ is a phenyl group, naphthyl group or thienyl group each of which may optionally be substituted;
$R^4$ is a carboxyl group or a group convertible to a carboxyl group in vivo;
n is an integer of 3 to 15;
or a hydroquinone derivative thereof and a pharmaceutically acceptable carrier or diluent.

The present invention also provides a method of treating or preventing allergic rhinitis in a mammal in need thereof which comprises administering to such mammal an effective amount of a compound of the formula (Ia) or a hydroquinone derivative thereof.

DETAILED DESCRIPTION OF THE INVENTION

Preferably, both of $R^1$ and $R^2$ are a methyl group.

Examples of the naphthyl group represented by $R^3$ in the above formula (Ia) include 1- or 2-naphthyl. Examples of the thienyl group represented by $R^3$ include 2- or 3-thienyl. $R^3$ is preferably optionally substituted phenyl or thienyl, more preferably phenyl. Each of the phenyl, naphthyl and thienyl represented by $R^3$ may have 1 to 3 substituents at a possible position in the ring. Examples of the substituent include lower alkyl having 1 to 4 carbon atoms such as methyl, ethyl, n-propyl, i-propyl, n-butyl; lower alkoxy having 1 to 4 carbon atoms such as methoxy, ethoxy, n-propoxy, i-propoxy; halogen atoms such as fluorine, chlorine and bromine; hydroxyl; methylenedioxy; and trifluoromethyl. In particular, the substituent is preferably lower alkyl or halogen, more preferably fluoro or methyl.

In particular, $R^3$ is preferably phenyl, 3- or 4-methylphenyl, 3- or 4-fluorophenyl, 2-thienyl or 3-thienyl.

Examples of the group convertible to a carboxyl group in vivo represented by $R^4$ include methyl, optionally substituted hydroxymethyl, and optionally esterified or optionally amidated carboxyl. Examples of the optionally substituted hydroxymethyl include unsubstituted hydroxymethyl, methoxymethyloxy, acetoxymethyl, nitroxymethyl and aminocarbonyloxymethy. Examples of the esterified carboxyl include lower alkoxycarbonyl having 2 to 8 carbon atoms (e.g., methoxycarbonyl, ethoxycarbonyl, benzyloxycarbonyl, pivaloyloxymethoxycarbonyl, etc.). Examples of the amidated carboxyl include aminocarbonyl, hydroxyaminocarbonyl, monoalkylaminocarbonyl having 2 to 4 carbon atoms (e.g., methylaminocarbonyl, ethylaminocarbonyl, etc.), dialkylaminocarbonyl having 3 to 5 carbon atoms (e.g., dimethylaminocarbonyl, etc.), cyclic aminocarbonyl (e.g., morpholinocarbonyl, thiomorpholinocarbonyl, etc.).

$R^4$ is preferably a carboxyl group or hydroxymethyl group.

n is preferably an integer of 5 to 9.

The hydroquinone derivative of a compound of the formula (Ia) means a compound of the formula (Ib):

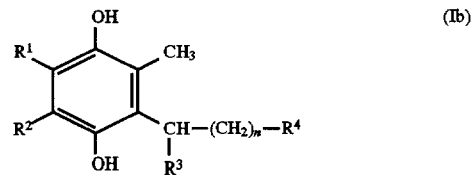

(Ib)

wherein each symbol is as defined above.

The compounds (Ia) and (Ib) to be used as an active ingredient of the present invention are described in U.S. Pat. No. 5,180,742 (JP-A 61-44840) or JP-A 63-101322 and can be prepared by the processes described therein. For example, the compound (Ib) can be prepared by reacting the corresponding hydroquinone compound without the asymmetric side chain with a compound of the formula: $CH(OH)R^3$—$(CH_2)_n$—$R^4$ in the presence of an acid catalyst. The compound (Ia) can be prepared by oxidizing the compound (Ib).

Biochemical interconversion between the quinone derivative of the above formula (Ia) and the hydroquinone derivative of the formula (Ib) is possible in vivo. These compounds can be considered to be physiologically and pharmacologically equivalent.

$R^4$ must be a free carboxyl group for expression of the activity of the compounds (Ia) and (Ib) in in vitro experiments. On the other hand, in in vivo experiments, therapeutic and prophylactic activity against allergic rhinitis is shown when $R^4$ is carboxyl or a group convertible into carboxyl by in vivo oxidation (e.g., ω-oxidation, β-oxidation) or hydrolysis.

Preferred examples of the compounds of the formula (Ia) or (Ib) to be used as an active ingredient in the present invention include those wherein $R^3$ is phenyl, 3- or 4-methylphenyl, 3- or 4-fluorophenyl, 2-thienyl or 3-thienyl, $R^4$ is carboxyl or hydroxymethyl, and n is an integer of 5 to 9. In particular, 7-(3,5,6-trimethyl-1,4-benzoquinon-2-yl)-7-phenylheptanoic acid is preferred.

The compounds of the formula (Ia) or (Ib) exist as their R- or S-isomers, and both isomers are included in the scope of the present invention. When $R^3$ is an aryl group such as phenyl or naphthyl, R-isomers are preferred in terms of their pharmacological activity.

The compounds to be used as an active ingredient in the present invention have low toxicity. For example, when (±)-7-(3,5,6-trimethyl-1,4-benzoquinon-2-yl)-7-phenylheptanoic acid (1000 mg/kg) was orally administered to a group of five ICR male mice (5 weeks old), no mice died for 7 days from the administration. The compound to be used as an active ingredient in the present invention can be used as it is or as a pharmaceutical composition (e.g., tablets, granules, capsules including soft capsules and microcapsules, liquid preparations, injections, suppositories, nasal drops, eye drops, etc.) prepared by mixing the compound with a per se known pharmaceutically acceptable carrier, diluent, excipient, etc., for treating or preventing allergic rhinitis, particularly nasal congestion in a mammal. The administration route may be oral or parenteral. The dose varies with the subject to be administered, administration route, symptoms, etc. For example, for oral administration to an adult patient, a unit dose of normally about 0.1 mg/kg to 20 mg/kg body weight, preferably 0.1 mg/kg to 10 mg/kg body weight is advantageously administered about once or twice a day.

The compounds (Ia) and (Ib) to be used as an active ingredient in the present invention have a hindered group at the α-carbon of the side chain of the quinone ring or hydroquinone ring, and the α-carbon atom is an asymmetric center. Either optical isomer due to the asymmetry specifically exhibits potent pharmacological activity. However even the racemic modification causes no pharmacological problem.

The compound to be used as an active ingredient in the present invention has a hindered group at the α-carbon atom of the side chain and is therefore hardly inactivated by in vivo metabolism. Therefore it can maintain its effective blood level for a long term and exhibit excellent pharmacological activity in a low dose.

Thus the pharmaceutical composition comprising a compound of the formula (Ia) or (Ib) of the present invention exhibits excellent antirhinitis activity against allergic rhinitis.

The following reference example, experiments and examples illustrate the present invention in detail but are not to be construed to limit the scope thereof.

Reference Example 1

Effects on the binding of U-46619 (11-9-epoxymethane-PGH$_2$, a substance having thromboxane A$_2$-like activity) to human platelet-derived TXA$_2$ receptor expressing cells Method:

A vector containing cDNA encoding TXA$_2$ receptor (TXA$_2$•R) and a vector containing cDNA encoding dihydrofolate reductase were mixed in a ratio of 10:1, and are transferred simultaneously to Chinese hamster ovary (CHO) cells by the calcium phosphate method. Two days later, these cells were inoculated into a medium containing 0.3 mM proline, 10% bovine fetus serum and 0.1 µM methotrexate in a concentration of 2000 cells/well and incubated. After 3 weeks, the grown colonies were subjected to receptor assay to obtain the transformant TCHO-25 having significantly higher U-46619 binding ability than that of the nontransformed CHO cells.

[$^3$H]-labelled U-46619 (12.5 nM) and various concentrations of (±)-7-(3,5,6-trimethyl-1,4-benzoquinon-2-yl)-7-phenylheptanoic acid (hereinafter referred to as Compound 1) were simultaneously added to the TXA$_2$•R expressing cell strain TCHO-25, and TXA$_2$•R binding inhibiting activity was determined by receptor assay.

Results:

The dissociation constant of U-46619 based on TXA$_2$•R on TCHO-25 cells was $3.1 \times 10^{-8}$ M, and the number of receptors on TCHO-25 cells was about $3 \times 10^5$/cell. Compound 1 competitively inhibited the binding of U-46619 to TXA$_2$•R, and the 50% inhibitory concentration was $6 \times 10^{-8}$ M.

Experiment 1

Inhibitory effects on allergic experimental rhinitis in guinea pigs

Hartley male guinea pigs weighing 350 to 450 g were used. Aerosol of 1% ovalbumin (OA) in physiological saline was prepared using an ultrasonic nebulizer and administered to the guinea pigs by inhalation for 10 minutes. Thus the guinea pigs were sensitized. One week later, the antigen was administered again by inhalation, and the guinea pigs were used for this experiment after one week. The following experiment procedures were carried out by reference to the method of Kojima et al. (Allergy, Vol. 35, p. 180–187 (1986)).

The sensitized guinea pigs were anesthetized by administering pentobarbital (30 mg/kg) intraperitoneally. The trachea was opened, a polyethylene tube connected to an infusion pump was inserted into the nasal side of the opened trachea, and physiological saline was perfused in the nasal cavity at a flow rate of 0.25 ml/min. 5% pontamine sky blue 6B (1 ml/kg body weight) was injected into a cervical artery, and physiological saline was perfused for 10 minutes (p-1). Then an antigen solution (0.3% OA) was perfused for 10 minutes (p-2), as was physiological saline for 40 minutes (p-3 to p-6). The collected sample was centrifuged at 3000 rpm for 10 minutes, and the absorbance of the supernatant at 620 nm was measured with a spectrophotometer to calculate the pigment concentration.

The drug was suspended in 5% gum arabic (G.A.) solution and was orally administered 1 hour before the antigen induction. The inhibitory ratio (%) was calculated as a ratio of the amount of the leaked pigment to the maximum amount of the leaked pigment in the control group 10 minutes after the antigen induction. The results are in Table 1.

TABLE 1

| Compound | Dose (mg/kg) | Number of animals | Inhibitory ratio (%) |
|---|---|---|---|
| Compound 1 | 30 | 9 | 58 |
| Mepyramine | 30 | 9 | 81 |

Thus the efficacy of Compound 1 in this experiment was confirmed. Further, the dose-dependence of Compound 1 was examined in a similar manner to that described above. The results are in Table 2.

TABLE 2

| Compound | Dose (mg/kg) | Number of animals | Inhibitory ratio (%) |
|---|---|---|---|
| 5% G.A. | — | 9 | — |
| Compound 1 | 0.3 | 10 | 29 |
| Compound 1 | 3 | 10 | 51* |
| Compound 1 | 30 | 10 | 73** |
| Mepyramine | 30 | 10 | 77** |

*$P < 0.05$, **$P < 0.01$ (Comparison with the 5% G.A. group, Dunnett assay)

Experiment 2

Effects of perfusion in nasal cavities on allergic rhinitis in guinea pigs

Aerosol of 1% ovalbumin (OA) solution in physiological saline was prepared using an ultrasonic nebulizer (TUR-3200, Nippon Kohden, Tokyo, Japan), and administered to Hartley male guinea pigs weighing 300 to 350 g (Seiwa Jikken Dohbutsu, Fukuoka, Japan) by inhalation for 10 minutes in a polyacrylamide box (20×28×20 cm) once a week (twice in all). Thus the guinea pigs were sensitized. One week after the sensitization, the guinea pigs were anesthetized with pentobarbital sodium (30 mg/kg, i.p.) and fixed on their backs on a thermal pad (Deltaphase isothermal pad, Braintree Scientific, Inc.). The cervical part was opened along the median line, the trachea was opened, a trachea cannula was inserted into the pulmonary side, and the esophagus was ligated. On the other hand, a polyethylene tube (5.5 cm in length, 2.3 mm in outer diameter, Hibiki) connected to an infusion pump was inserted at the nasal side into the choana. To prevent leakage of the perfusion solution into the oral cavity, the oral cavity was stuffed with absorbent cotton impregnated with glycerin, and the absorbent cotton was bonded with an adhesive (Aron alpha, trade name). A suspension of the drug (5 mg/kg) in 5% gum arabic (G.A.) was perfused in the nasal cavity at a flow rate of 0.25 ml/min for 10 minutes. Then 5% pontamine sky blue solution (1 ml/kg) in physiological saline was injected into a cervical vein, physiological saline was perfused for 10 minutes, and the perfusion solution was collected (Period-1). Then 0.3% OA in physiological saline was perfused for 10 minutes (Period-2). Then physiological saline was perfused again for 20 minutes, and the perfusion solution was collected every 10 minutes (Periods-3 and 4). The resulting perfusion solution was centrifuged at 15,000× g for 1.5 minutes, and the amount of the pigment in the supernatant was determined by absorbance at 610 nm. The activity of the drug was evaluated using as an indication the increased amount of the leaked pigment at Period-3 (i.e., (the amount of the pigment at Period-3)—(the amount of the pigment at Period-1)). The results are in Table 3.

TABLE 3

| Compound | Dose (mg/kg) | Number of animals | Pigment concentration (µg/ml) | Inhibitory ratio (%) |
|---|---|---|---|---|
| 5% G.A. | — | 16 | 13.83 ± 2.61 | — |
| Compound 1 | 5 | 16 | 8.87 ± 2.47 | 36 |

Experiment 3

Effects on increase of permeability of nasal mucosal blood vessels induced by U-46619 in guinea pigs Hartley male guinea pigs (body weight: 300 to 400 g, Nippon SLC, Shizuoka, Japan) were anesthetized with pentobarbital (30 mg/kg, i.p.). The trachea was opened, a trachea cannula was inserted into the pulmonary side, and a polyethylene tube connected to an infusion pump (Terumo Corporation) was inserted into the nasal side. To prevent leakage of the perfusion solution, the oral cavity was stuffed with absorbent cotton impregnated with glycerin. Physiological saline was perfused in the nasal cavity at a flow rate of 0.25 ml/min, and effluent liquid from the nose was collected for 10 minutes (Period-0). Then 5% pontamine sky blue solution (1 mg/kg) in physiological saline was injected into a cervical vein, and likewise the perfusion solution was collected for 10 minutes (Period-1). Then a solution of U-46619 in physiological saline was perfused for 10 minutes, and the perfusion solution was collected (Period-2). Then physiological saline was perfused again for 40 minutes, and the perfusion solution was collected every 10 minutes (Periods-3, 4, 5, 6). This perfusion solution was centrifuged at 3000 rpm for 10 minutes, and the amount of the pigment in the supernatant was determined with absorbance at 620 nm. Compound 1 was suspended in 5% gum arabic solution and orally administered one hour before the perfusion of the U-46619 solution. Activity of the drug was evaluated using as an indication an amount of the leaked pigment at Period-3. The results are in Table 4.

TABLE 4

| Compound | Dose (mg/kg) | Number of animals | Inhibitory ratio (%) |
|---|---|---|---|
| 5% G.A. | — | 4 | — |
| Compound 1 | 0.3 | 6 | 40 |
| Compound 1 | 1 | 6 | 67** |
| Compound 1 | 3 | 6 | 71** |
| Compound 1 | 30 | 6 | 82** |

**$P < 0.01$ (Comparison with the 5% G.A. group, Dunnett assay)

Experiment 4

Effects on intranasal pressure increase induced by U-46619 in guinea pigs

Hartley male guinea pigs weighing 300 to 400 g (Nippon SLC, Shizuoka, Japan) were anesthetized with pentobarbital (30 mg/kg, i.p.) and fixed on their backs. The cervical part was opened along the median line, the trachea was opened for maintaining respiration, and a cannula was inserted. A tube (JMS cutdown tube, 2.5 mm in outer diameter and 3.5 cm in length) was inserted from the opened site of the trachea into the nasal cavity. The other end of the tube was connected to a respirator (Harvard respirator, model 683), and air was sent into the nasal cavity at a tidal volume of 4 ml and a respiration rate of 70/min. Aerosol of U-46619 (30 µg/ml) solution was prepared using an ultrasonic nebulizer and sent into the nasal cavity for 3 minutes. Changes of the intranasal pressure were determined with a differential pressure transducer connected to the branch of the tube. To prevent air leakage into the oral cavity, the oral cavity was closed with an adhesive (Aron alpha, trade name).

Compound 1 was orally administered 1 hour before the U-46619 treatment. The results of this experiment are in Table 5.

TABLE 5

| Compound | Dose (mg/kg) | Number of animals | Inhibitory ratio (%) after 10 min. | after 20 min. |
|---|---|---|---|---|
| 5% G.A. | — | 7 | — | — |
| Compound 1 | 0.003 | 8 | 32 | 18 |
| Compound 1 | 0.01 | 8 | 17 | 38 |
| Compound 1 | 0.03 | 8 | 62** | 72** |
| Compound 1 | 0.1 | 8 | 82** | 64** |

*$P < 0.05$, **$P < 0.01$ (Comparison with the 5% G.A. group, Dunnett assay)

Experiment 5

Effects on intranasal pressure increase induced by inhalation of antigens in actively sensitized (involving IgE participation) guinea pigs Hartley male guinea pigs weighing 300 to 400 g (Nippon SLC, Shizuoka, Japan) were immunized by a modified method of the method of Levine et al. Sensitization was carried out by intraperitoneally administering physiological saline (1 ml) containing ovalbumin (OA)(10 μg) and aluminium hydroxide gel (5 mg) 4 times every 2 weeks. The sensitized guinea pigs were used one week after the final administration. These guinea pigs were anesthetized with pentobarbital (30 mg/kg, i.p.). In a similar manner to that described in Experiment 4, changes of intranasal pressure were determined. Aerosol of OA (3%) was prepared using an ultrasonic nebulizer provided between the respirator and the intranasal tube, and sent into the nasal cavity for 3 minutes. The test drug was suspended in 5% G.A. solution and orally administered one hour before the OA inhalation. The results of this experiment are in Table 6.

TABLE 6

| Compound | Dose (mg/kg, p.o.) | Number of animals | Internasal pressure increase AUC(0–30 min) | Inhibitory ratio (%) |
|---|---|---|---|---|
| 5% G.A. | — | 12 | 339 ± 55 | — |
| Compound 1 | 0.3 | 12 | 208 ± 44 | 39 |
| Compound 1 | 3.0 | 12 | 241 ± 32 | 3.0 |
| Compound 1 | 30 | 13 | 183 ± 36* | 46 |
| Azelastine hydrochloride | 1.0 | 8 | 92 ± 14** | 73 |

*$P < 0.05$, **$P < 0.01$ (Comparison with the 5% G.A. group, Dunnett assay)

Experiment 6

Effects on intranasal pressure increase induced by antigen inhalation in guinea pigs sensitized by antigen inhalation Aerosol of 1% OA solution in physiological saline was prepared and administered to Hartley male guinea pigs weighing 300 to 400 g (Nippon SLC, Shizuoka, Japan) by inhalation for 10 minutes. One week later, inhalation was performed again for sensitization. These animals were used as sensitized animals. In a similar manner to that described in Experiment 4, intranasal pressure was determined. The test drug was suspended in 5% G.A. solution and orally administered one hour before the antigen induction. The results of this experiment are in Table 7.

TABLE 7

| Compound | Dose (mg/kg, p.o.) | Number of animals | Increase of intranasal pressure AUC(0–25 min) | Inhibitory ratio (%) |
|---|---|---|---|---|
| 5% G.A. | — | 7 | 278 ± 35 | — |
| Compound 1 | 0.3 | 7 | 246 ± 44 | 12 |
| Compound 1 | 3.0 | 8 | 201 ± 41 | 28 |
| Compound 1 | 30 | 7 | 143 ± 19* | 49 |
| Azelastine hydrochloride | 1.0 | 7 | 157 ± 35** | 44 |

*$P < 0.05$ (Comparison with the 5% G.A. group, Dunnett assay)

Experiment 7

Effects on increase of permeability of nasal mucosal blood vessels by intranasal antigen-perfusion in actively sensitized (involving IgE participation) guinea pigs A solution of OA (1 mg) in physiological saline (1 ml) was intramuscularly administered in divided portions to both femoral parts of Sprague-Dawley male rats weighing about 250 g (7 weeks old, Nippon Clea) according to the method of Mota et al. At the same time, killed Bordetella pertussis ($2 \times 10^{10}$) was administered intraperitoneally as an adjuvant. The rats were used as IgE-sensitized animals 12 to 14 days after the sensitization. The rats were anesthetized with pentobarbital (30 mg/kg, i.p.). The trachea was opened, a trachea cannula was inserted into the pulmonary side of the opened trachea according to the method of Kojima et al. On the other hand, a polyethylene tube connected to an infusion pump (Terumo Co.) was inserted into the nasal side. Physiological saline was perfused in the nasal cavity at a flow rate of 0.2 ml/min, and the effluent solution from the nasal rostrum was collected for 10 minutes. To prevent leakage of the perfusion solution to the oral cavity, the oral cavity was closed using an adhesive (Aron alpha, trade name). Then 4% pontamine sky blue solution in physiological saline was injected into a tail vein in an amount of 0.5 ml/100 g body weight, and the perfusion solution was collected for 10 minutes in a similar manner. Then an antigen solution (0.3% OA) was perfused for 10 minutes, and the perfusion solution was collected. This perfusion solution was centrifuged at 3000 rpm for 10 minutes, and the amount of the pigment in the supernatant was determined from the absorbance at 620 nm. The drug was suspended in 5% G.A. solution and orally administered one hour before the antigen perfusion. The amount of the pigment leaked to the antigen perfusion solution was used as an indication to evaluate the activity of the drug. The results of this experiment are in Table 8.

TABLE 8

| Compound | Dose (mg/kg) | Number of animals | Inhibitory ratio (%) |
|---|---|---|---|
| 5% G.A. | — | 18 | — |
| Compound 1 | 10 | 19 | 49* |
| Compound 1 | 100 | 19 | 83** |

*$P < 0.05$, **$P < 0.01$ (Comparison with the 5% G.A. group, Dunnett assay)

Experiment 8

Effects of Compound 1 on nasal allergy in guinea pigs sensitized by antigen inhalation—evaluation using an MRI (Magnetic Resonance Imaging) system Method:

Aerosol of 1% OA solution in physiological saline was prepared and administered to Hartley male guinea pigs weighing 300 to 400 g (Nippon SLC, Shizuoka, Japan) by inhalation for 10 minutes. One week later, inhalation was performed again for sensitization. These animals were used as sensitized animals. The sensitized animals were anesthetized with ketamine (50 mg/kg, i.m.) and xylazine (5 mg/kg, i.m.), and two catheters were inserted into the tail side and the rostral side of the trachea. The catheter at the rostral side was inserted near the entrance of the nasopharynx. After insertion of the catheters, physiological saline or 0.3% OA solution was put through the rostral catheter into the nasal end, and the guinea pigs were allowed to stand for 10 minutes. Then the nasal cavity was washed with 3 ml of physiological saline, air (10 ml) was blown into the catheter 10 times to remove the residual liquid, and the guinea pigs were subjected to MRI. Compound 1 was suspended in 5% G.A. solution and orally administered one hour before the antigen stimulation.

The choanal sectional area was determined using IBAS (image analysis system). The data were analyzed statistically by the student's t-test.

Results:

The choanal sectional area in the group (8 guinea pigs) stimulated by antigens decreased significantly relative to that in the physiological saline treated group (8 guinea pigs)($85.1\pm6.7$ mm$^2$→$56.6\pm3.1$ mm$^2$, $-33.6\%$, $P<0.01$). In the group (8 guinea pigs) of oral administration of Compound 1 (30 mg/kg), the decrease of the choanal sectional area by antigen stimulation was inhibited significantly. The inhibitory ratio was 48% ($P<0.05$).

Example 1

Preparation of tablets

Tablets each containing 40 mg of the active ingredient were prepared according to conventional methods. The formulation of the tablet is as follows:

| | |
|---|---|
| ($\pm$)-7-(3,5,6-Trimethyl-1,4-benzoquinon--2-yl)-7-phenylheptanoic acid | 40.0 mg |
| Hydroxypropylcellulose | 3.6 |
| Magnesium stearate | 0.4 |
| Corn starch | 18.0 |
| Lactose | 58.0 |
| Total | 120.0 mg |

Example 2

Preparation of tablets

Tablets each containing 80 mg of the active ingredient were prepared according to conventional methods. The formulation of the tablet is as follows:

| | |
|---|---|
| ($\pm$)-7-(3,5,6-Trimethyl-1,4-benzoquinon--2-yl)-7-phenylheptanoic acid | 80.0 mg |
| Hydroxypropylcellulose | 5.0 |
| Magnesium stearate | 0.5 |
| Corn starch | 24.5 |
| Lactose | 50.0 |
| Total | 160.0 mg |

Example 3

Preparation of granules

Granules containing the active ingredient (10%) were prepared according to conventional methods. The formulation of the granules is as follows:

| | |
|---|---|
| ($\pm$)-7-(3,5,6-Trimethyl-1,4-benzoquinon--2-yl)-7-phenylheptanoic acid | 100.0 mg |
| Hydroxypropylcellulose | 30.0 |
| Carmellose calcium | 30.0 |
| Talc | 10.0 |
| Poloxamer 188 | 20.0 |
| Crystalline cellulose | 70.0 |
| Corn starch | 300.0 |
| Lactose | 440.0 |
| Total | 1000.0 mg |

What is claimed is:

1. A method of treating or preventing allergic rhinitis in a mammal in need thereof which comprises administering to such mammal an effective amount of a compound of the formula (Ia):

$$\text{(Ia)}$$

wherein $R^1$ and $R^2$ are each independently a methyl group or methoxy group, or $R^1$ and $R^2$ are linked together to form —CH=CH—CH=CH—;

$R^3$ is a phenyl group, naphthyl group or thienyl group each of which is unsubstituted or substituted with at least one member selected from the group consisting of alkyl of 1–4 carbon atoms, alkoxy of 1–4 carbon atoms, halogen, hydroxy, methylenedioxy and trifluoromethyl;

$R^4$ is a carboxyl group or a hydroxymethyl group;

n is an integer of 3 to 15;

or a hydroquinone derivative thereof.

2. A method according to claim 1, wherein both of $R^1$ and $R^2$ are a methyl group.

3. A method according to claim 1, wherein $R^3$ is a phenyl group which is unsubstituted or substituted with at least one substituent selected from lower alkyl groups and halogen.

4. A method according to claim 1, wherein $R^3$ is phenyl, 3-fluorophenyl, 4-fluorophenyl, 3-methylphenyl, 4-methylphenyl, 2-thienyl or 3-thienyl.

5. A method according to claim 1, wherein n is an integer of 5 to 9.

6. A method according to claim 1, wherein the quinone derivative is 7-(3,5,6-trimethyl-1,4-benzoquinon-2-yl)-7-phenylheptanoic acid.

* * * * *